United States Patent [19]

Wampler

[11] Patent Number: 4,625,712

[45] Date of Patent: Dec. 2, 1986

[54] HIGH-CAPACITY INTRAVASCULAR BLOOD PUMP UTILIZING PERCUTANEOUS ACCESS

[75] Inventor: Richard K. Wampler, Rancho Cordova, Calif.

[73] Assignee: Nimbus, Inc., Rancho Cordova, Calif.

[21] Appl. No.: 537,244

[22] Filed: Sep. 28, 1983

[51] Int. Cl.⁴ .............................................. A61F 1/24
[52] U.S. Cl. .............................. 128/1 D; 128/DIG. 3; 604/151; 604/264; 604/266; 604/52; 415/DIG. 4; 623/3
[58] Field of Search ................... 128/1 D, DIG. 3; 604/151, 264, 267; 27/24.1, 24 A, 24 R; 415/212 A, 213 C, DIG. 4, 122 A, 122 R, 140; 623/3

[56] References Cited

U.S. PATENT DOCUMENTS

| | | | |
|---|---|---|---|
| 967,512 | 8/1910 | Gregory et al. | 415/212 A |
| 2,328,199 | 8/1943 | Day | 27/24 A |
| 3,021,793 | 2/1962 | Bolstad | 604/151 |
| 3,614,953 | 10/1971 | Moss | 604/35 |
| 3,667,069 | 6/1972 | Blackshear et al. | 128/1 D |
| 3,720,200 | 3/1973 | Laird | 128/1 D |
| 3,877,838 | 4/1975 | Choy | 128/1 D |
| 4,077,394 | 3/1978 | McCurdy | 128/1 D |
| 4,135,253 | 1/1979 | Reich et al. | 415/DIG. 4 |
| 4,173,796 | 11/1979 | Jarvik | 623/3 |
| 4,310,930 | 1/1982 | Goldowsky | 623/3 |
| 4,382,199 | 5/1983 | Isaacson | 623/3 |
| 4,417,850 | 11/1983 | Hacker et al. | 415/213 C |

FOREIGN PATENT DOCUMENTS

| | | | |
|---|---|---|---|
| 2423673 | 11/1975 | Fed. Rep. of Germany | 128/1 D |
| 0034409 | 3/1977 | Japan | 415/213 C |
| 0733417 | 12/1951 | United Kingdom | 415/140 |

OTHER PUBLICATIONS

Medical Societies, Feb. 14, 1959, p. 347, Hall, J. E.

*Primary Examiner*—Stephen C. Pellegrino
*Assistant Examiner*—Mark Rooney
*Attorney, Agent, or Firm*—Weissenberger and Peterson

[57] ABSTRACT

Full-flow cardiac assist is provided for cardiogenic shock patients without major surgery by a miniature axial-flow pump which can be inserted into the heart through the femoral artery and driven via a flexible cable from an external power source. The cable is contained within the catheter attached to the pump. The catheter also provides a conduit to supply the pump bearings with a blood-compatible purge fluid at a rate and pressure sufficient to prevent thrombus formation and introduction of blood elements between rotating and stationary elements of the pump. Due to the very small diameter of the pump, rotational speeds on the order of 10,000 to 20,000 rpm can be used to produce a blood flow on the order of about four liters per minute without significant hemolysis.

6 Claims, 6 Drawing Figures

HIGH-CAPACITY INTRAVASCULAR BLOOD PUMP UTILIZING PERCUTANEOUS ACCESS

This invention relates to blood pumps, and more particularly to a miniature blood pump capable of percutaneous insertion into the vascular system to provide full-flow right or left ventricular temporary cardiac assist without major surgery.

BACKGROUND OF THE INVENTION

The medical profession is frequently confronted with cases of cardiogenic shock (i.e. a condition in which the heart still functions but is not pumping sufficient blood to keep the patient alive). Emergency treatment of this condition often requires some form of cardiac assist which maintains a blood flow sufficient for survival while other measures are initiated to restore the heart itself to more normal function.

At the present time, the only methods available for a cardiac assist of this nature are pump systems whose connection to the vascular system involves major surgery, or a balloon catheter inserted into an appropriate artery. Unfortunately, major surgery may involve too much delay or risk for a patient in cardiogenic shock, and the balloon catheter may not provide sufficient improvement in cardiac output.

It has been proposed to provide left-sided circulatory support by the use of non-thoracotomy vascular access. In such systems, two simultaneous arterial sites would be employed to pump blood from the heart into the arterial system. However, this technique would necessitate the use of long, small-bore cannulae which would result in large pressure drops. Exposure of conduits with negative pressure could result in air embolism and serious complications. In addition, the subclavian artery would need to be employed for the pump inlet because of its proximity to the heart. Surgical access to this vessel is more difficult than for the femoral artery.

Use of an external pump for support of the right heart would require access at two simultaneous venous sites. In this case the pump output would need to be returned by a long, small-bore cannula to the pulmonary artery. Similar complications of large pressure drops with negative pressures and possible air embolism could occur. The prior art has thus been unable to provide an easily-implemented low-risk circulatory-assist device capable of rapidly providing full flow heart assist to critically ill patients.

SUMMARY OF THE INVENTION

The invention solves the problems of the prior art by providing a high-speed miniature blood pump, preferably of the axial type, which is small enough to directly access either the right or left heart for circulatory assistance by means of either the peripheral venous or arterial system. This device is intended for peripheral percutaneous insertion and is capable of providing as much as three to four liters of flow per minute.

Support of the right heart would involve an antegrade insertion through the tricuspid and pulmonary valve into the pulmonary artery. Such a procedure would be possible from peripheral venous access through either the femoral, external jugular or cephalic vein.

Support of the left heart would be achieved by retrograde insertion through the aortic valve into the left ventricle. This could be performed from either the subclavian or femoral artery.

In the event that peripheral access proves difficult, it would be possible to achieve vascular access by means of a mini-thoracotomy and introduction through the ventricular apex.

The pump of this invention is driven by a small power unit on the outside of the body, by way of a flexible cable or hydraulic line extending through a small diameter cannula at the site of systemic circulatory access.

In order to deliver the required blood flow, the pump of this invention has to operate with a shaft speed of 10,000 to 20,000 rpm. Pumps of such high rotational speed have previously been thought unsuitable for blood pumping applications because it was generally thought that the tips of the impeller blades passing close to the stationary wall of the impeller chamber would create shear forces so great as to cause severe hemolysis. The present invention arises out of the recognition that the linear velocity of the tips of the blades is dependent upon the diameter of the pump, and is therefore small enough in a miniature pump as contemplated by this invention to produce no significant hemolysis even at the speeds required for its operation.

Thrombus formation is avoided in the pump of this invention by the use of a purge seal between the rotating and stationary parts of the pump. In addition, bacteriostatic effects may be achieved by using ethanol, or a similar bacteriostatic agent capable of acting as a bearing lubricant, as the purge fluid.

It is thus the object of the invention to provide a high-capacity miniature blood pump which can rapidly access the heart for cardiac assist purposes through the vascular system without major surgery and at low risk to the patient.

It is another object of this invention to provide a pump of the type described which is antithrombogenic.

DESCRIPTION OF THE PREFERRED EMBODIMENT

Figure 1B:
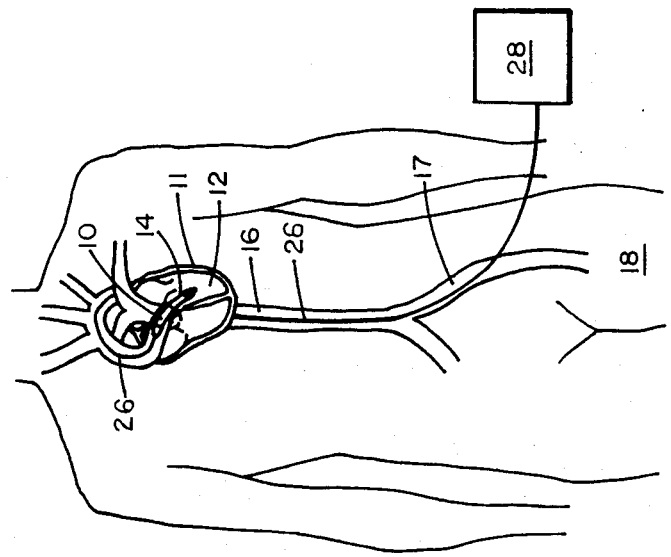
FIG. 1b is a schematic view of a human being illustrating the insertion of the pump of this invention through the femoral artery.

The intravascular blood pump 10 of this invention may access the left ventricle 12 (FIG. 1a) of the heart 11 by retrograde insertion of an appropriate short, flexible inlet cannula 14 through the aortic valve 15. The cannula 14 is guided through the aorta 16 from the femoral artery 17 (FIG. 1b), into which it can advantageously be inserted in the thigh 18. In the operation of the pump 10, blood is pumped in the direction of the arrows (FIG. 1a) from the left ventricle 12 through the inlet element 19 of cannula 14 and the interior of cannula 14 into the pump 10. At the outlet of pump 10, the pumped blood is discharged through outlet element 20 into the aorta 16.

Although the pump of this invention is discussed herein in terms of a left ventricle assist by retrograde insertion through the femoral artery, it will be understood that it could also be used without significant modification as a left or right heart assist through other insertion techniques if desired, as discussed above.

The pump 10 is preferably driven by a flexible shaft 24 extending through a catheter 26 placed into the femoral artery 17 and aorta 16. The catheter 26 also serves as a conduit for a purge fluid whose purpose and function will be described below. Instead of the shaft 24, a hydraulic system using the catheter 26 may equally well be used to provide motive power to the pump 10.

Figure 1A:
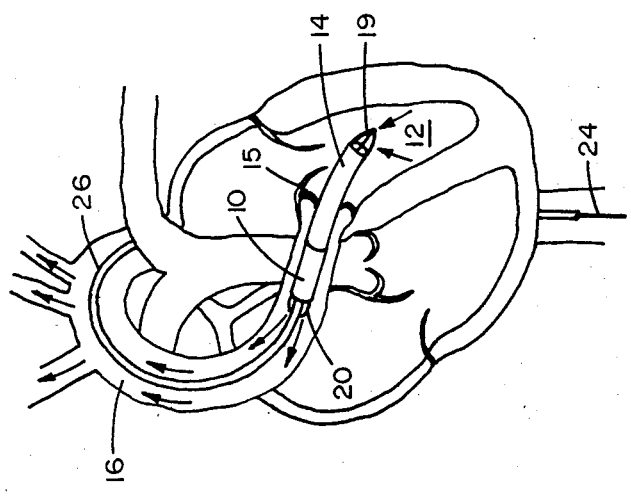
FIG. 1a is a schematic section of a human heart generally in the plane of the aorta, illustrating a preferred positioning of the pump of this invention for cardiac assist purposes.

In the arrangement of FIGS. 1a and b, an appropriate support unit 28 located outside the patient's body provides the drive power for the shaft 24, and also provides the purge fluid to the pump 10 through the catheter 26. The catheter 26 is sufficiently small in diameter to allow relatively unobstructed blood flow around it when it is inserted into an artery.

Figure 2:
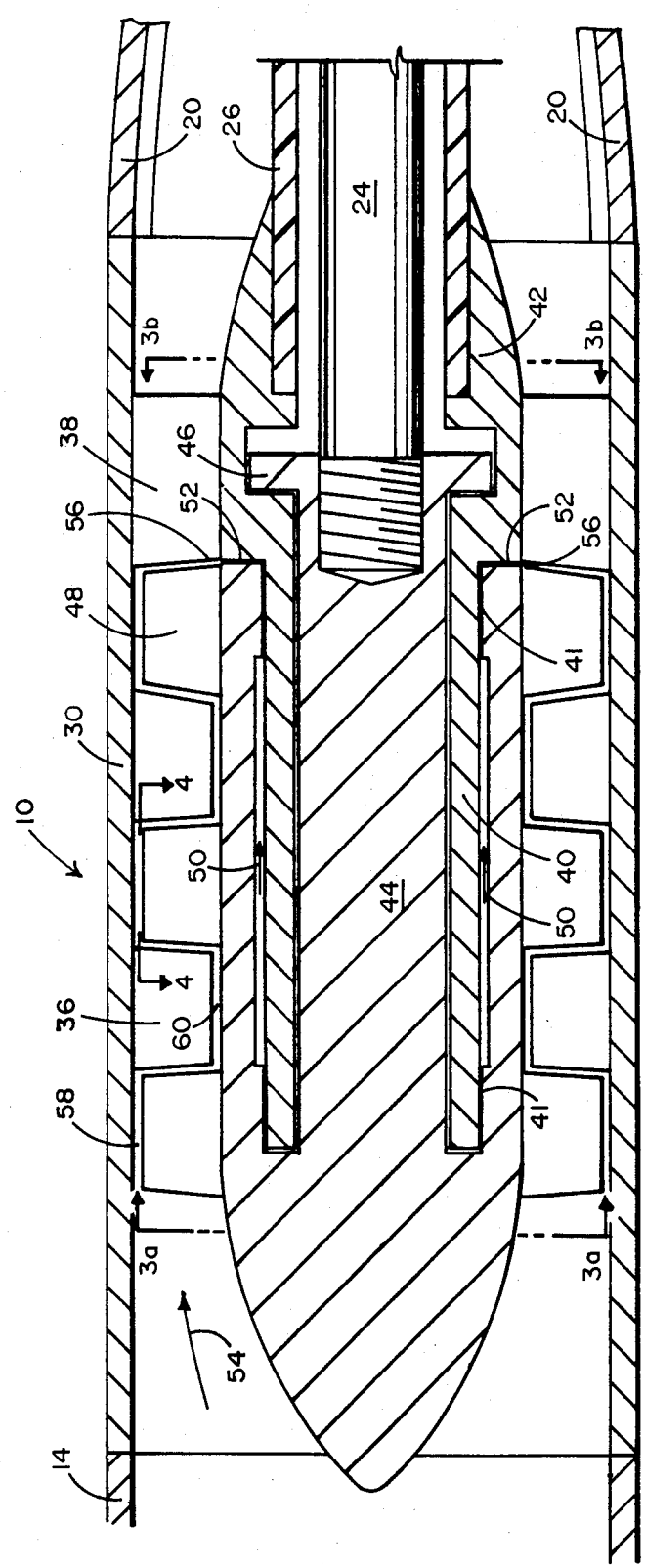
FIG. 2 is a partially schematic axial cross section of the pump of this invention.

Turning now to FIG. 2, the pump 10 has a housing 30 which is generally cylindrical along the body of the pump 10. The outlet element 14 and outlet element 20 are tapered to facilitate insertion and withdrawal of the pump 10 through the vascular system of the patient. The housing 30 carries stator blades 36. Support struts 38 (which also act as stator blades) connect the housing 30 to the stator support bearing 40 and tube attachment cone 42.

Figure 3B:
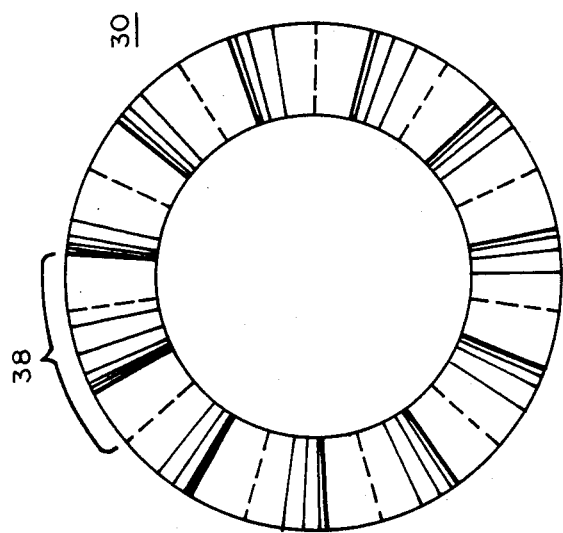
FIGS. 3a and 3b are fragmentary transverse sections of the pump of FIG. 2 along lines 3a—3a and 3b—3b in FIG. 2.
Figure 4:
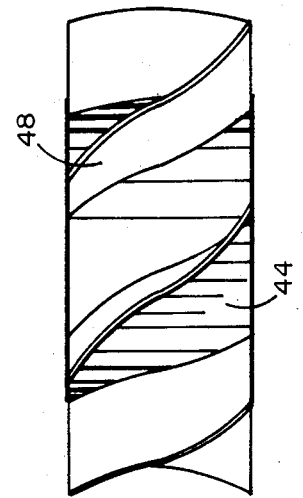
FIG. 4 is a fragmentary section of the pump of FIG. 2 along line 4—4 in FIG. 2.
Figure 3A:
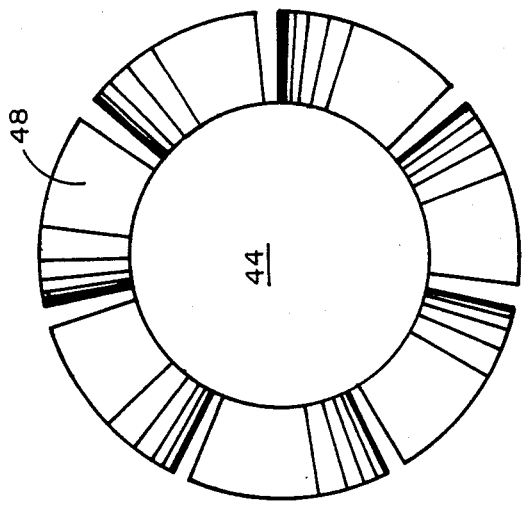

The cylindrical stator hub 40 supports the rotor 44 for rotational movement as driven by cable 24. Axial movement of the rotor 44 is prevented by bearing flange 46. The rotor 44 carries a series of rotor blades 48 whose curved cross section (best shown in FIG. 4) is similar to that of the stator blades 36. However, the number of rotor blades in each ring of blades is different from the number of stator blades in each ring (there may be, for example, seven rotor blades per ring and eleven stator blades per ring), as best illustrated in FIG. 3.

The journal bearings 41 are lubricated by a continuous flow of purge fluid 50 which is introduced into the pump 10 under pressure through the catheter 26. The purge fluid 50 flows through the face seal 52 and is eventually discharged into the blood stream 54 at interface 56. As described in the copending application Ser. No. 537,243, filed Sept. 28, 1983, and entitled ANTI-THROMBOGENIC BLOOD PUMP, thrombus formation in pump 10 is prevented by maintaining a sufficient outflow of purge fluid 50 along the annular interface 56 to prevent blood elements from contacting the rotor and stator surfaces at the interface 56.

The pump of this invention must of necessity be extremely small. Its outer diameter should ideally not exceed 7 to 9 mm. In order to provide the required blood flow on the order of four liters per minute, the pump of this invention needs to operate at speeds on the order of 10,000 to 20,000 rpm. In the operation of the pump, annular areas of blade tip shear occur at 58 and 60 in FIG. 2 where the tips of the blades 38 and 48 continuously sweep close to the rotor 44 and housing 30, respectively. However, in the worst case, which occurs in the area 58, the extremely small dimension of the pump causes the relative motion of the tip of blade 48 with respect to housing 30 to remain below 5 m/sec. This relative velocity is low enough in combination with adequate tip clearance (on the order of 0.1 mm) to maintain the shear forces in space 58 at a level sufficiently low to create no undue hemolysis. There is even less damage to the red cell membranes in space 60, as the relative velocity between the stator blade 38 and the rotor 44 is smaller because space 60 is closer to the axis of pump 10 than space 58.

It will be seen that the present invention provides an efficient, intravascular cardiac assist method and apparatus which can be rapidly applied and removed without surgery and with minimal risk to the patient.

I claim:

1. A method providing high-volume cardiac assist without major surgery, comprising the steps of:
   (a) inserting continuous rotary pumping means into a living vascular system to be wholly contained thereby; and
   (b) operating said pumping means to generate a flow of blood through said pumping means and said vascular system.

2. An intravascular blood pump, comprising:
   (a) an elongated housing open at each end, said housing having a shape and size allowing it to be passed through a human blood vessel;
   (b) non-hemolytic rotary pumping means within said housing for pumping blood in a living patient longitudinally through said housing;
   (c) conduit means extending from said housing and adapted to lie within said blood vessel without blocking it;
   (d) power means located remotely from said pumping means for powering said pumping means; and
   (e) drive means including a flexible cable extending from said power means to said pumping means through said conduit means for transferring drive power from said power means to said pumping means.

3. The pump of claim 2, in which said rotary pumping means is an axial flow pump operating at a rotational speed on the order of 10,000–20,000 rpm.

4. The pump of claim 2, in which said rotary pumping means has a blood flow rate on the order of four liters per minute.

5. The pump of claim 2, in which said rotary pumping means is an axial pump in which the relationship between speed of rotation and blade size is such that no point on any blade has a linear velocity high enough to cause significant hemolysis.

6. The pump of claim 5, in which said speed of rotation exceeds 10,000 rpm.

* * * * *